United States Patent
Santamaria-Pang et al.

(10) Patent No.: US 10,740,651 B2
(45) Date of Patent: Aug. 11, 2020

(54) METHODS OF SYSTEMS OF GENERATING VIRTUAL MULTI-DIMENSIONAL MODELS USING IMAGE ANALYSIS

(71) Applicant: General Electric Company, Schenectady, NY (US)

(72) Inventors: Alberto Santamaria-Pang, Schnectady, NY (US); Daniel Eugene Meyer, Rexford, NY (US); Michael Ernest Marino, Niskayuna, NY (US); Qing Li, Niskayuna, NY (US); Dmitry V. Dylov, Niskayuna, NY (US); Aritra Chowdhury, Troy, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 245 days.

(21) Appl. No.: 15/796,379

(22) Filed: Oct. 27, 2017

(65) Prior Publication Data

US 2018/0121760 A1 May 3, 2018

Related U.S. Application Data

(60) Provisional application No. 62/413,684, filed on Oct. 27, 2016.

(51) Int. Cl.
*G06K 9/00* (2006.01)
*G06K 9/62* (2006.01)
(Continued)

(52) U.S. Cl.
CPC ............ *G06K 9/6256* (2013.01); *G06K 9/44* (2013.01); *G06K 9/6267* (2013.01);
(Continued)

(58) Field of Classification Search
CPC ...... G06K 9/6256; G06K 9/44; G06K 9/6267; G06K 9/6274; G06K 2209/05; G06T 7/11;
(Continued)

(56) References Cited

U.S. PATENT DOCUMENTS

| 2006/0171585 A1 | 8/2006 | Rinck et al. |
| 2012/0323547 A1* | 12/2012 | Baloch ................... G16H 50/50 703/11 |

(Continued)

FOREIGN PATENT DOCUMENTS

WO     2015150320 A1    10/2015

OTHER PUBLICATIONS

Miguel ("Three-dimensional synthetic blood vessel generation using stochastic I-systems," In: Proceedings vol. 8669, SPIE Medical Imaging 2013: Image Processing <DOI: 10.1117/12.2007532>, sections 1-4, pp. 1-6) in view of Wu (U.S. PG-PUB No. 2014/0341426) (Year: 2014).*

(Continued)

*Primary Examiner* — Ping Y Hsieh
(74) *Attorney, Agent, or Firm* — Fletcher Yoder, P.C.

(57) ABSTRACT

The present approach relates to the use of trained artificial neural networks, such as convolutional neural networks, to classify vascular structures, such as using a hierarchical classification scheme. In certain approaches, the artificial neural network is trained using training data that is all or partly derived from synthetic vascular representations.

20 Claims, 14 Drawing Sheets

(51) Int. Cl.

| | |
|---|---|
| *G06N 3/08* | (2006.01) |
| *G06N 3/04* | (2006.01) |
| *G09B 23/30* | (2006.01) |
| *G06T 7/00* | (2017.01) |
| *G16H 50/20* | (2018.01) |
| *G06K 9/44* | (2006.01) |
| *G06T 7/11* | (2017.01) |
| *G06T 7/155* | (2017.01) |
| *G16H 50/50* | (2018.01) |

(52) U.S. Cl.
CPC .......... *G06K 9/6274* (2013.01); *G06N 3/04* (2013.01); *G06N 3/08* (2013.01); *G06T 7/0012* (2013.01); *G06T 7/11* (2017.01); *G06T 7/155* (2017.01); *G09B 23/30* (2013.01); *G09B 23/303* (2013.01); *G16H 50/20* (2018.01); *G16H 50/50* (2018.01); *G06K 2209/05* (2013.01); *G06N 3/0454* (2013.01); *G06N 3/084* (2013.01); *G06T 2200/04* (2013.01); *G06T 2207/10056* (2013.01); *G06T 2207/10064* (2013.01); *G06T 2207/30016* (2013.01); *G06T 2207/30101* (2013.01); *G06T 2207/30172* (2013.01)

(58) Field of Classification Search
CPC ... G06T 7/155; G06T 7/0012; G06T 2200/04; G06T 2207/10056; G06T 2207/10064; G06T 2207/30016; G06T 2207/30101; G06T 2207/30172; G16H 50/50; G16H 50/20; G06N 3/08; G06N 3/04; G06N 3/0454; G06N 3/084; G09B 23/30; G09B 23/303

See application file for complete search history.

(56) References Cited

U.S. PATENT DOCUMENTS

| | | | |
|---|---|---|---|
| 2014/0032197 A1* | 1/2014 | Kang | G16B 5/00 703/11 |
| 2014/0254899 A1* | 9/2014 | Dai | G06T 7/11 382/128 |
| 2014/0341426 A1* | 11/2014 | Wu | G06T 7/187 382/103 |
| 2016/0100632 A1 | 4/2016 | Sharma et al. | |
| 2016/0106321 A1 | 4/2016 | Sharma et al. | |
| 2016/0148372 A1 | 5/2016 | Itu et al. | |
| 2019/0130578 A1* | 5/2019 | Gulsun | G06N 3/0454 |

OTHER PUBLICATIONS

Galarreta-Valverde, Miguel A., et al.; "Three-Dimensional Synthetic Blood Vessel Generation Using Stochastic L-Systems", SPIE Medical Imaging 2013, vol. 8669, 2013, pp. 1-5.

International Search Report Written Opinion, PCT/US2017/058825; dated Jul. 2, 2018, pp. 1-16.

International Search Report Written Opinion, PCT/US2017/058825; dated May 9, 2019, pp. 1-12.

* cited by examiner

METHODS OF SYSTEMS OF GENERATING VIRTUAL MULTI-DIMENSIONAL MODELS USING IMAGE ANALYSIS

CROSS-REFERENCE TO RELATED APPLICATION

This application claims priority to and the benefit of Provisional Application No. 62/413,684, entitled "METHODS OF SYSTEMS OF GENERATING VIRTUAL MULTI-DIMENSIONAL MODELS USING IMAGE ANALYSIS", filed Oct. 27, 2016, which is herein incorporated by reference in its entirety.

BACKGROUND

Characterizing the morphology of vasculature in digital pathology is a useful step in defining the microenvironment within brain tissue samples. In particular, understanding the geometry of vessel configuration and its changes during a disease may provide insight into the progression of neuropathological degenerative diseases such as Alzheimer's disease.

Deep learning requires abundant training data for tuning the large number of parameters of the various inherent models. If a certain class is imbalanced then the classification models could become prone to biased outcomes. However, acquisition of natural training samples is a time consuming and labor intensive process.

BRIEF DESCRIPTION

This work explores the concept of generating virtual multi-dimensional data from a parametric representations, such as a representation of vasculature, using pre-trained convolutional neural networks. In certain embodiments, the multi-dimensional data may be three dimensional. The motivation behind pre-trained convolutional neural networks is that the method bypasses the pipeline of image segmentation and hand engineered feature extraction. Thus in certain embodiments, a method to characterize the morphology is provided by taking both the shape and intensity information into account. Shown is an ability to distinguish between the different morphologies.

Thus, is certain embodiments, virtually generated 3D parametric models of vasculature are capable of representing the morphology of naturally acquired data. In one embodiment, the method is applied to three distinct morphologies that are abundantly observed in formalin-fixed, paraffin-embedded brain tissue samples: single blood vessels showing no (or collapsed) lumen (RoundLumen−); single blood vessels with distinct lumen (RoundLumen+); two blood vessels occurring together in close proximity (Twins). The method involves extraction of features using pre-trained convolutional neural networks. A hierarchical classification is performed to distinguish between single blood vessels (RoundLumen) and Twins; followed by a more granular classification between RoundLumen− and RoundLumen+. A fair comparison of the results is performed between the virtually generated and natural data. Classification models built on the virtual data perform well, accuracies of 92.8% and 98.3% for the two classification tasks respectively was achieved.

In certain embodiments, the method is used to characterize blood vessel morphology in neuropathology.

In one embodiment, a method is provided for generating a multi-dimensional synthetic vascular model. In accordance with this method, a set of control points is defined in a three-dimensional coordinate system. The control points are interpolated between to generate a skeleton of a synthetic blood vessel being generated. A three-dimensional volume of the synthetic blood vessel is generated about the skeleton.

In a further embodiment, a method if provided for training and using an artificial neural network. In accordance with this method, a training data set of images is generated. At least a portion of the images are derived by taking slices through one or more synthetic vessels of a synthetic vascular model. The training data set of images is provided to an artificial neural network to generate a trained neural network. An input set of clinical images is provided to the trained neural network for classification of vascular features within the set of clinical images. An output is received from the trained neural network based on the classifications generated for the set of clinical images.

In an additional embodiment, a vascular morphology classification neural network is provided. In accordance with this embodiment, the neural network includes: an input layer configured to receive images depicting sectional views of one or more vascular vessels in a biological sample; two or more hidden layers trained using synthetic vessel images to classify morphological features present in the sectional views of the biological sample; and an output layer downstream from the hidden layers, wherein the output layer is configured to provide an output based on the classifications generated for the morphological features.

BRIEF DESCRIPTION OF DRAWINGS

These and other features, aspects, and advantages of the present invention will become better understood when the following detailed description is read with reference to the accompanying drawings in which like characters represent like parts throughout the drawings.

FIG. 6 depicting a rendered version of the 3D image, in accordance with aspects of the present disclosure;

FIG. 10 depicting a non-linear model of twins, in accordance with aspects of the present disclosure;

DETAILED DESCRIPTION

Figure 1:
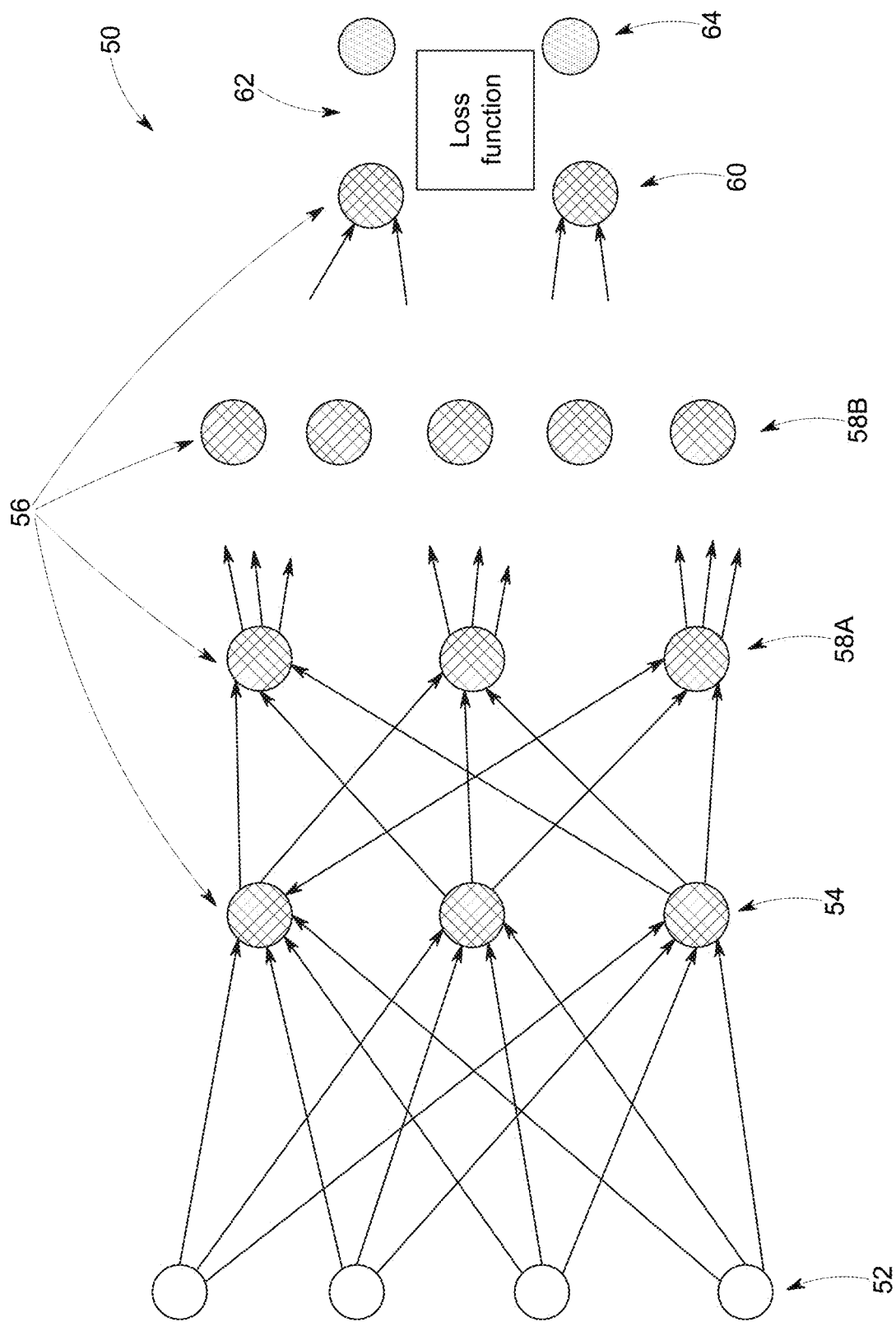
FIG. 1 depicts an example of an artificial neural network for training a deep learning model, in accordance with aspects of the present disclosure.
Figure 2:
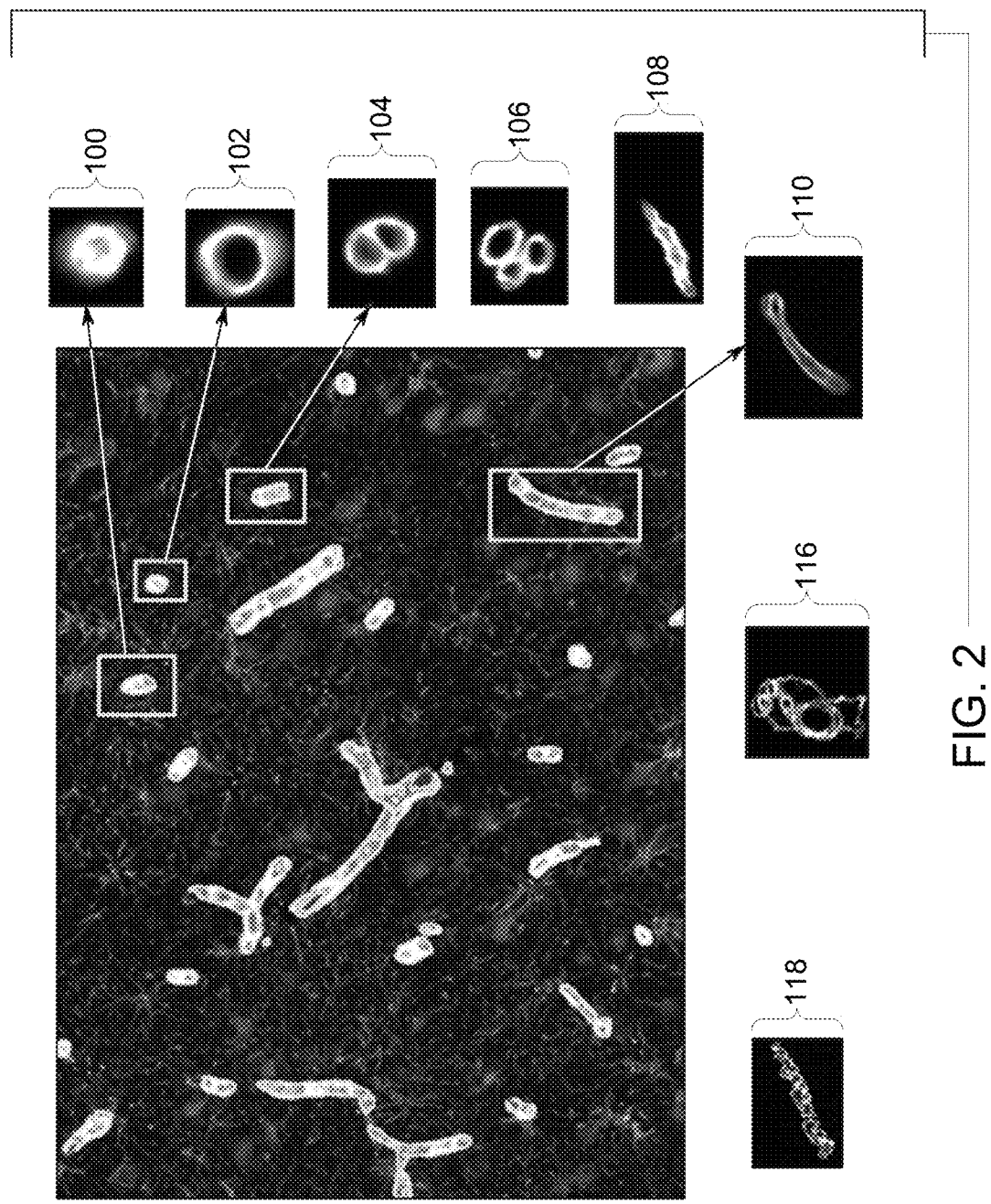
FIG. 2 depicts different morphologies in the natural data with respect to a multichannel image, overlaid with different protein markers, in accordance with aspects of the present disclosure.
Figure 3:
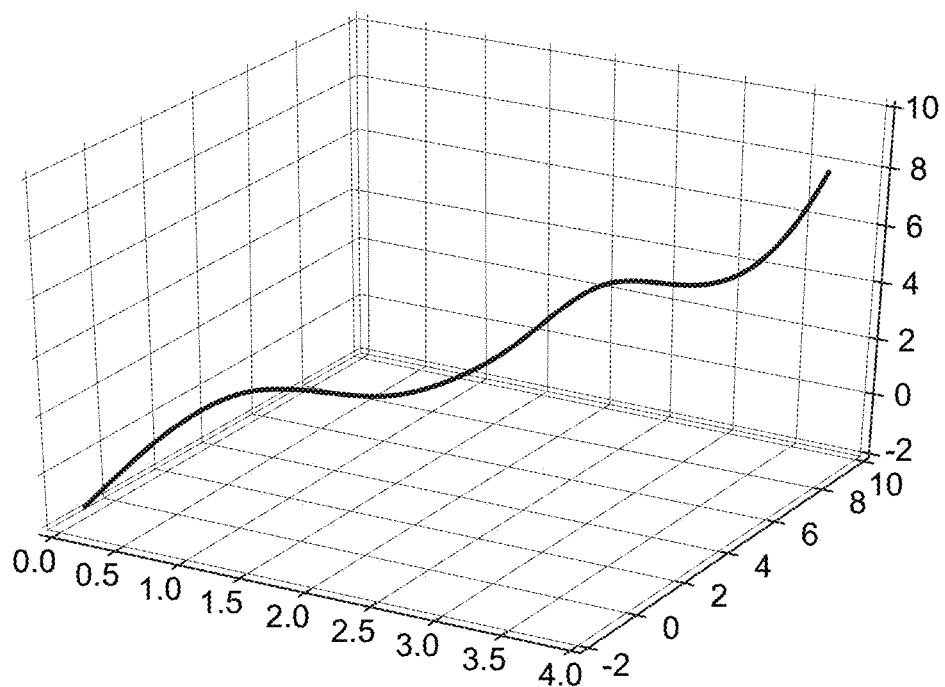
FIGS. 3-6 depict steps in the development of a 3D synthetic model in accordance with one implementation, with FIG. 3 depicting a center line of a synthetic blood vessel, FIG. 4 depicting examples of a disk rotation for defining vessel boundaries, FIG. 5 depicting the generated 3D image in the form of an array.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure While aspects of the following discussion are provided in the context of analysis of medical data, it should be appreciated that the present techniques are not limited to such medical contexts. Indeed, the provision of examples and explanations in such a medical context is only to facilitate explanation by providing instances of real-world implementations and applications. However, the present approaches may also be utilized in other suitable data analysis contexts, such as to generate, represent, or analyze other multi-dimensional structures or environments in a synthetic form and to use the synthetic representation to train a neural network. Thus, in general, the present approaches may be useful in any data analysis context where interpretability of artificial neural network outputs is desired, such as to facilitate selection of one or more features of interest in the relevant analytic context.

By way of example, characterizing the morphology of vasculature in digital pathology is a useful step in defining the microenvironment within brain tissue samples. In particular, understanding the geometry of vessel configuration and its changes during a disease may provide insight into the progression of neuropathological degenerative diseases such as Alzheimer's disease. The present approach characterizes different types of blood vessel morphologies which are found in relative abundance in typical image data sets. Examples of these blood vessel morphologies include, among others; singular blood vessels with no visible lumen, singular blood vessels with a distinct lumen, and blood vessels appearing as a pair, respectively referred to herein as RoundLumen−, RoundLumen+, and Twins.

As discussed herein, convolutional neural networks (CNN) may be used to characterize blood vessels, as opposed to using traditional image processing techniques which involve segmentation and hand-crafted feature extraction. By way of example, a pre-trained CNN may be used to extract features from the images. This technique of "deep transfer learning" may be compared to the visual bag of words (VBW) method for feature extraction. As may be appreciated, acquisition of naturally-occurring samples for training a CNN may be a time consuming and labor intensive process. Deep learning requires abundant training data for tuning the large number of parameters of the various inherent models. If a certain class is imbalanced then the classification models could become prone to biased outcomes. The construction of three-dimensional (3D) parametric models, presented here, addresses these issues and creates a balanced high-fidelity classification model.

With this in mind, a basic 3D vasculature model was generated (e.g., a synthetic or virtual vasculature model) using knowledge of blood vessel geometry. The 3D vasculature was repeatedly sliced at various angles and orientations to obtain two-dimensional (2D) samples for training the machine learning model, thereby mimicking the physical sectioning of tissue during sample preparation for microscopy. In addition, a filtering technique was used to fine-tune the virtual data to reflect the variability present in the naturally acquired samples. In one study, three models were trained based, respectively, on: virtual data, natural data and a mixture of both. The models were tested on a reserved, independent portion of the naturally occurring data, with a hierarchical classification being performed to demonstrate a proof of concept.

In one study, a hierarchical approach was employed in which the first classification task involved distinguishing between singular blood vessels (RoundLumen) and pair of blood vessels (Twins). The second task was of finer granularity and involved the classification between RoundLumen− (i.e., no visible lumen) and RoundLumen+ (i.e., a discernible lumen). Classification metrics were determined for both classification tasks and it was observed that the artificial data improved upon a model trained from only the natural data. In particular, as discussed herein, classification models built on the synthetic data performed well, achieving accuracies of 92.8% and 98.3% for the two classification tasks respectively.

With the preceding introductory comments in mind, a brief introduction to machine learning approaches, such as artificial neural networks, suitable for use with the present approach is provided. Neural networks as discussed herein may encompass deep neural networks, fully connected networks, convolutional neural networks (CNNs), perceptrons, auto encoders, recurrent networks, wavelet filter banks, or other neural network architectures. These techniques are referred to herein as deep learning techniques, though this terminology may also be used specifically in reference to the use of deep neural networks, which is a neural network having a plurality of layers.

As discussed herein, deep learning techniques (which may also be known as deep machine learning, hierarchical learning, or deep structured learning) are a branch of machine learning techniques that employ mathematical representations of data and artificial neural network for learning. By way of example, deep learning approaches may be characterized by their use of one or more algorithms to extract or model high level abstractions of a type of data of interest. This may be accomplished using one or more processing layers, with each layer typically corresponding to a different level of data abstraction and, therefore potentially employing or utilizing different aspects of the initial data or outputs of a preceding layer (i.e., a hierarchy or cascade of layers) as the target of the processes or algorithms of a given layer. In a data analysis context, this may be characterized as different layers corresponding to the different feature levels or levels of abstraction in the data.

In general, the processing from one level or abstraction to the next can be considered as one 'stage' of the analysis process. Each stage of the analysis can be performed by separate neural networks or by different parts of one larger neural network. For example, as discussed herein, a single deep learning network may cover all stages in an analytic process (e.g., from an initial input to an output data set). Alternatively, separate distinct deep learning network(s) may each cover only one stage (or a subset of stages) of the overall analysis process.

As part of the initial training of deep learning processes to solve a particular problem, training data sets may be employed that have known initial values and known or desired values for a final output of the deep learning process. As discussed herein, in certain aspects of the present approach all or part of the training data may be virtual or synthetic images corresponding to vascular morphological structures, as opposed to derived from clinical data or images of naturally occurring vascular structures. That is, aspects of the training data in the present approach may be derived by taking two-dimensional sectional images or views of a three-dimensional synthetic model of vasculature.

The training of a single stage may have known input values corresponding to one representation space and known output values corresponding to a next-level representation space. In this manner, the deep learning algorithms may process (either in a supervised or guided manner or in an unsupervised or unguided manner) the known or training data sets until the mathematical relationships between the initial data and desired output(s) are discerned and/or the mathematical relationships between the inputs and outputs of each layer are discerned and characterized. Similarly, separate validation data sets may be employed in which both the initial and desired target values are known, but only the initial values are supplied to the trained deep learning algorithms, with the outputs then being compared to the outputs of the deep learning algorithm to validate the prior training and/or to prevent over-training.

With the preceding in mind, FIG. 1 schematically depicts an example of an artificial neural network 50 that may be trained as a deep learning model as discussed herein. In this example, the network 50 is multi-layered, with a training input 52 and multiple layers including an input layer 54, hidden layers 58A, 58B, and so forth, and an output layer 60 and the training target 64 present in the network 50. Each layer, in this example, is composed of a plurality of "neurons" or nodes 56. The number of neurons 56 may be constant between layers or, as depicted, may vary from layer to layer. Neurons 56 at each layer generate respective outputs that serve as inputs to the neurons 56 of the next hierarchical layer. In practice, a weighted sum of the inputs with an added bias is computed to "excite" or "activate" each respective neuron of the layers according to an activation function, such as rectified linear unit (ReLU), sigmoid function, hyperbolic tangent function, or otherwise specified or programmed. The outputs of the final layer constitute the network output 60 which, in conjunction with a target value or construct 64, are used to compute some loss or error function 62, which will be backpropagated to guide the network training.

The loss or error function 62 measures the difference between the network output 60 and the training target 64. In certain implementations, the loss function may be a mean squared error (MSE). Alternatively, the loss function 62 could be defined by other metrics associated with the particular task in question, such as a softmax function.

With the preceding in mind, the neural network 50 may be trained for use in the analysis of data in a manner that facilitates identification of vascular structures or features (or other suitable features in a medical or non-medical context), as discussed herein. In this manner, the present approach may be useful for characterizing the morphology of vasculature in digital pathology, which is one step in defining the microenvironment within brain tissue samples. This in turn may facilitate understanding the nature of vessel structure and how it changes during disease, which may provide insight into the progression of neuropathological degenerative diseases, such as Alzheimer's disease. For example, blood vessel density in a tissue sample could be indicative of neuronal activity in the brain.

With respect to the data provided to the trained neural network for analysis, one example of such data may be images of a biological sample with a specific morphology, such as vascular or neural network. In certain embodiments the images are acquired by fluorescence microscopy of brain tissues such as immunostained tissue for collagen IV. The stained tissue may be characterize by three different types of blood vessel morphologies which are found in relative abundance in the tissue samples.

In certain embodiments, the advantages of the present approach are two-fold. First, the present approach facilitates classification of blood vessels using convolutional neural networks (CNN) as opposed to traditional image processing techniques which involve segmentation and hand crafted feature extraction. In particular, as discussed herein, pre-trained convolutional neural networks were used to extract features from the images and this technique of using deep transfer learning was compared to the visual bag of words (VBW) method of feature extraction. The results demonstrated that the pre-trained CNN was able to distinguish the morphologies of blood vessels better than the standard VBW method.

Second, the present approach relies upon multi-dimensional (e.g., three-dimensional (3D)) virtual models (also referred to as synthetic models herein) of vasculature generated using parametric methods and based on knowledge of blood vessels geometry. This allows for generation of a more robust training set than might otherwise be obtained using conventional approaches. In particular, computational predictive diagnosis approaches benefit from access to a large amount of data for training the machine learning models. For example, deep learning requires training data for tuning the large number of parameters of the various models.

This is often inconsistent with the use of natural-occurring training samples, whose acquisition is typically via a time consuming and labor intensive process. Further, acquisition of naturally-occurring or clinical training data in a medical imaging context may be problematic because acquisition of tissue samples from a patient is necessarily invasive or post-mortem, and the subsequent preparation of the sample may alter the morphology being studied. In addition, the different classes of morphologies are inherently imbalanced and are not equally represented, which may be problematic from a training perspective.

By constructing and utilizing 3D parametric models, the imbalance and training set size issues are addressed. In one implementation, the 3D volumes are sliced at various degrees of freedom to obtain samples for training the machine learning model. A filtering technique may then be used to fine tune the synthetic data such that it captures the variability present in the naturally acquired samples. This approach allows for the modeling of vasculature using parametric 3D geometric methods in part or exclusively.

Natural Data

With the preceding in mind, it may be beneficial to provide examples of natural data so as to provide context as to the types of naturally-occurring structures being represented in the synthetic vascular data discussed herein. To provide this context, neuropathological tissue samples underwent multiplexed staining analysis and fluorescent imaging. This involved a cycling process of tissue sample staining with 2-3 dye-labeled antibodies, imaging, dye inactivation and repeated staining with a new set of dye-labeled antibodies. Images underwent illumination correction, registration and auto-fluorescence subtraction. Endothelial cell marker collagen IV for blood vessel associated stain is included as a structural marker for blood vessels. FIG. 1 depicts different morphologies in natural data with respect to a multichannel image overlaid with different protein markers. Various examples of different observed morphologies are depicted to the side of the image and include: round blood vessels with no lumen 100 (RoundLumen−), round blood vessels with single lumen 102 (RoundLumen+), twins 104, triplets 106, rods 108, hybrids 110, large-N families 116, and artifacts 118. The number of instances of different types of morphologies are depicted in Table 1.

TABLE 1

| Morphology | Frequency |
| --- | --- |
| RoundLumen− | 689 |
| RoundLumen+ | 3,427 |
| Twins | 266 |
| Rods | 3,358 |
| Hybrids | 221 |
| Triplets | 55 |
| Quadruples | 19 |
| Unidentifiables | 187 |
| Artifacts | 24 |
| Total | 8,246 |

Synthetic Data

With the preceding description of structures observed in natural data in mind, the following discussion relates one implementation of the generation of synthetic data that may be used to represent such structures in a neural network training operation. The development of the 3D synthetic model in accordance with this example is illustrated in FIGS. 3-6. In this example, the construction of the artificial model starts with defining a set of control points in three-dimensional Cartesian coordinates. The control points reflect the basic structure that the blood vessel is supposed to represent. Both linear and/or non-linear skeletons may be used. This is followed by interpolating between the points using a 3D cubic spline interpolator. This forms the skeleton or the center line that represents the center or the lumen of the blood vessel and is shown below in FIG. 3.

The 3D volume of the blood vessel is constructed after this step. A number of parameters are defined, such as: the inner radius of the blood vessel (r); the outer radius (R); the number of sampling points along the spline (N); and the number of sampling points in the radial direction (Nr).

At each sampling point; a circular disk is defined along the z-axis by randomly perturbing the values of r and R. Also defined is an intensity model for the blood vessels depicted in Equation (1). From the natural images, it appears that the intensity is high in the periphery of the blood vessel and decays towards the lumen and as the image moves away from the periphery. In certain embodiments, this model may use an exponential decay in the following form:

$$I(d) = I_{max} \exp(-\alpha |r'-d|) \quad (1)$$

where, $I_{max}$ is the maximum intensity, a is the calibration coefficient (in $mm^{-1}$ units) $r'=(R+r)/2$, and d is the distance from the center of the lumen.

Figure 4:
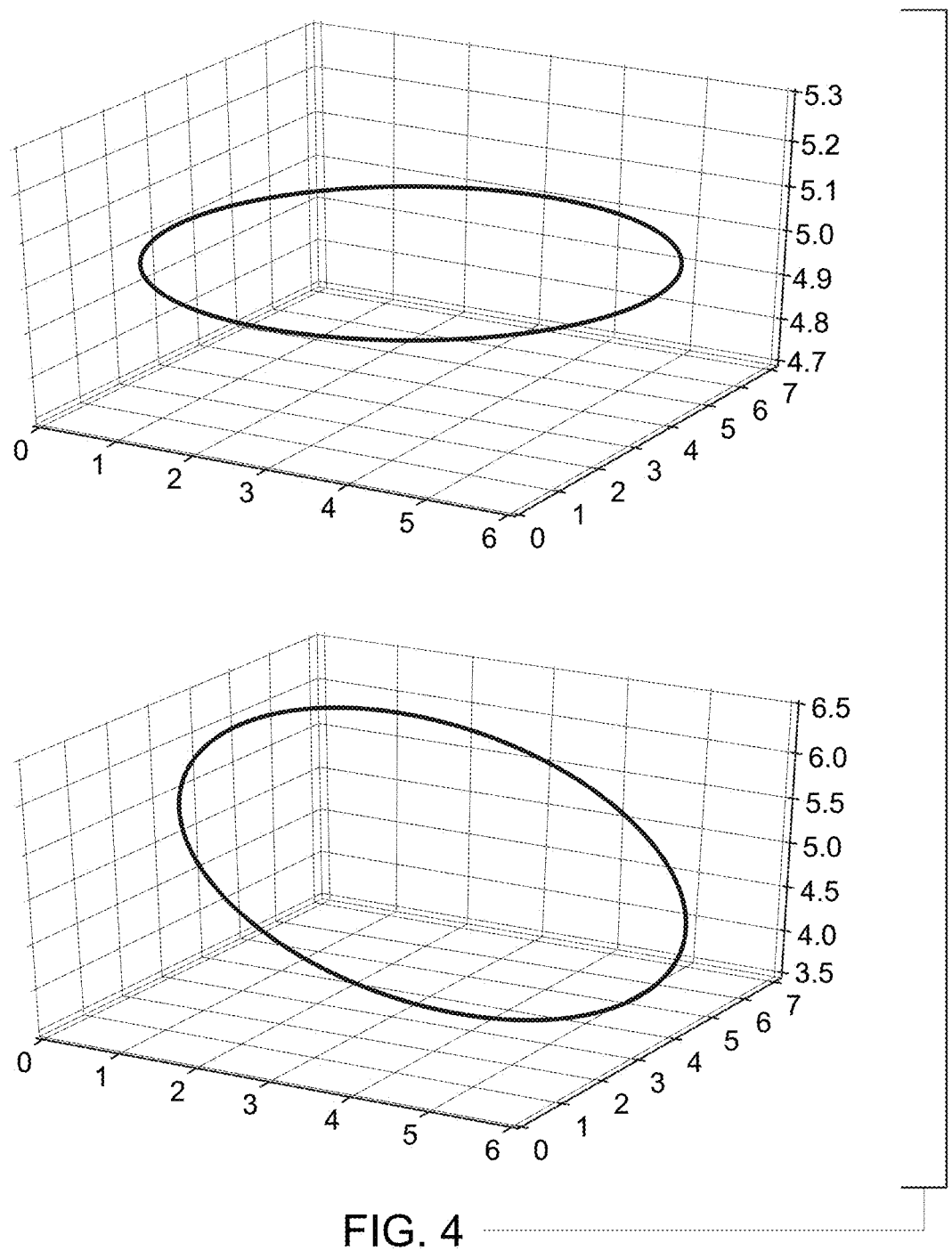
Figure 5:
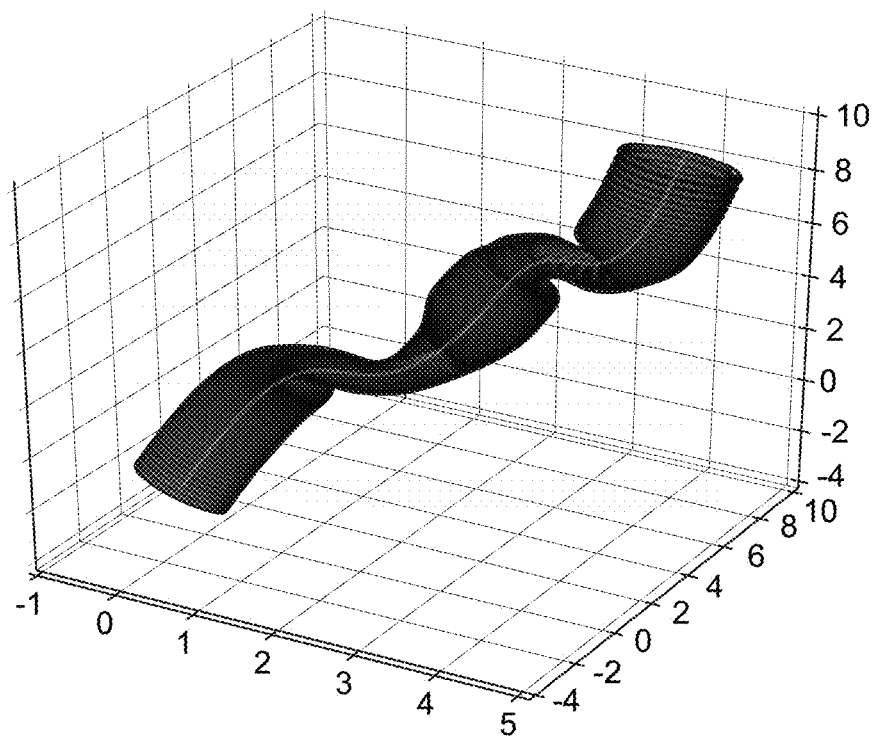
Figure 6:
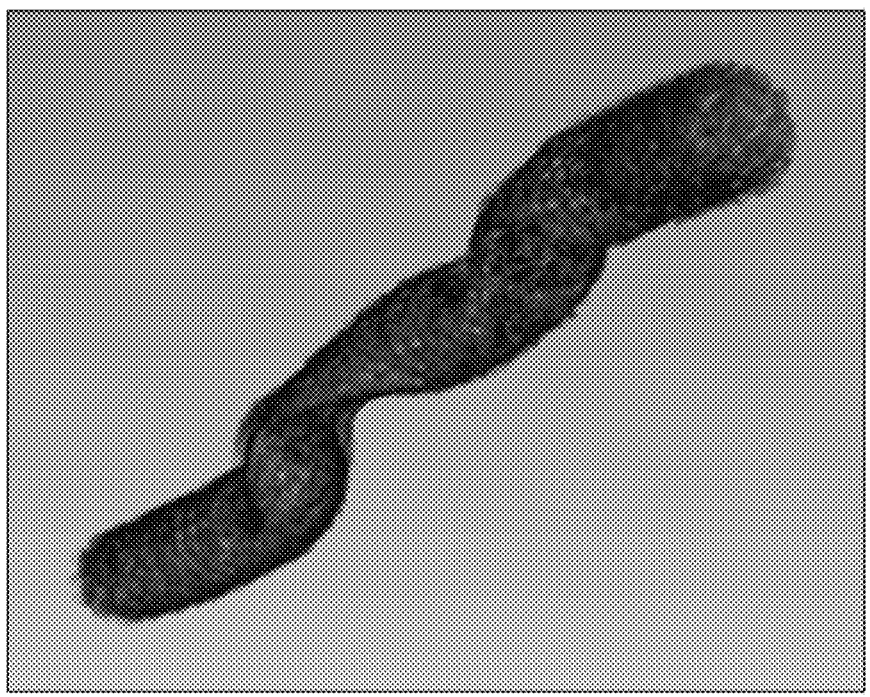

At each point on the disc, the voxel density is defined as a normal distribution with mean I(d) and standard deviation 0.01. This is followed by formulating the rotation matrix by calculating the angle between the tangent to the spline at that sampling point and the z-axis. The points corresponding to each point on the disc are therefore mapped or rotated along the curve by multiplying the coordinates with the rotation matrix. An example of this rotation is depicted in FIG. 4. The coordinates are discretized, such that an actual 3D image is obtained in the form of an array. This is depicted in FIG. 5. The intensity values are normalized and assigned to the corresponding discretized points in the three-dimensional array. The volume rendered version of the 3D image is depicted in FIG. 6. Therefore, just by changing the parameters of the model several different 3D images can be built and sliced at various angles to mimic the natural tissue cross sections at various depths and angles.

Figure 7:
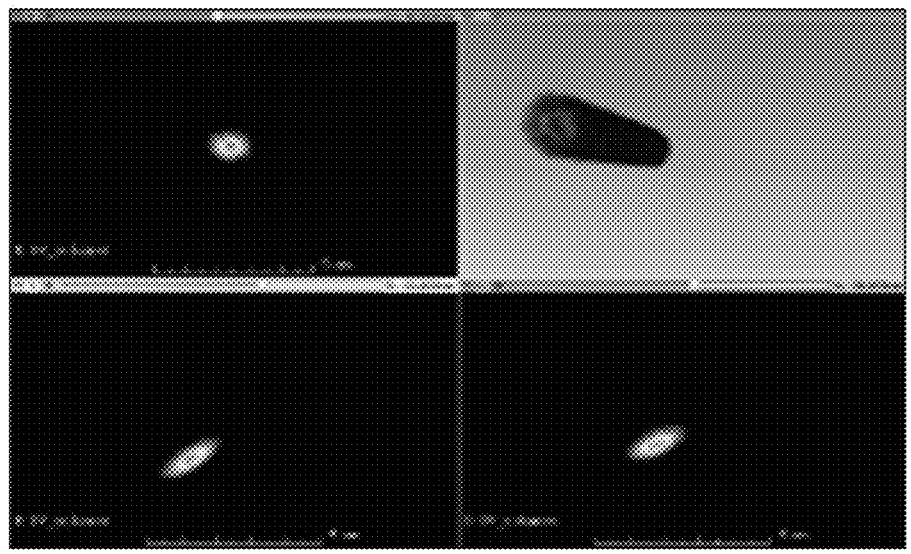
FIGS. 7-10 are 3D synthetic models and their corresponding projections along different planes of view in accordance with one implementation, with FIG. 7 depicting a linear model of RoundLumen−, FIG. 8 depicting a linear model of RoundLumen+, FIG. 9 depicting a non-linear model of RoundLumen+.
Figure 8:
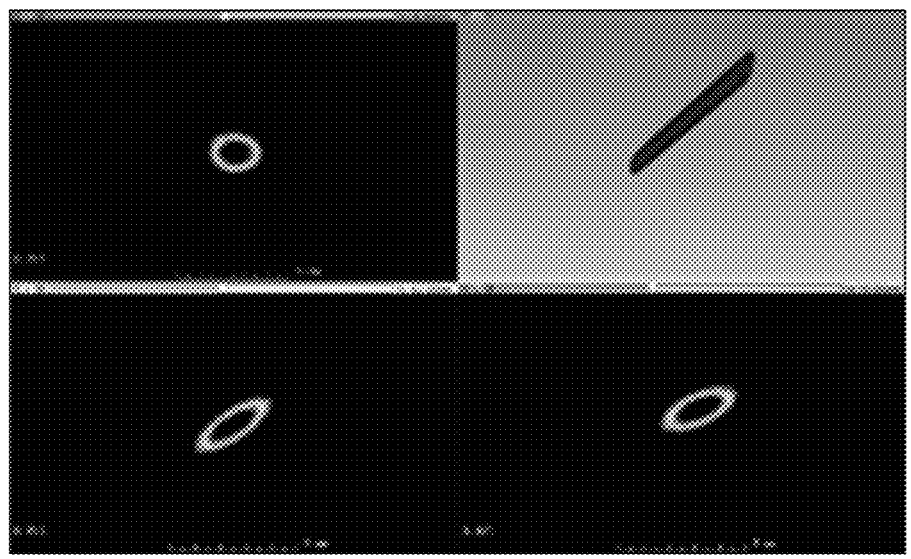
Figure 9:
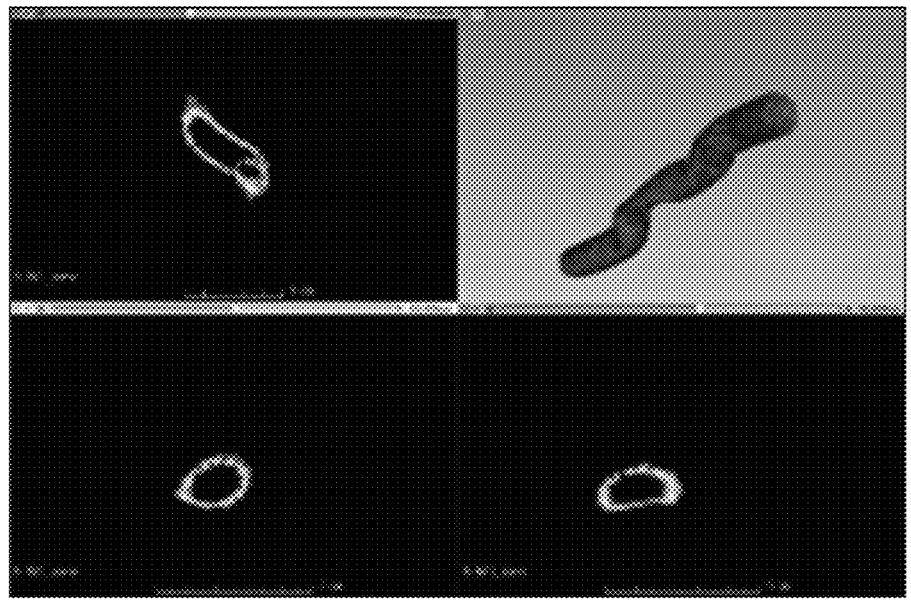
Figure 10:
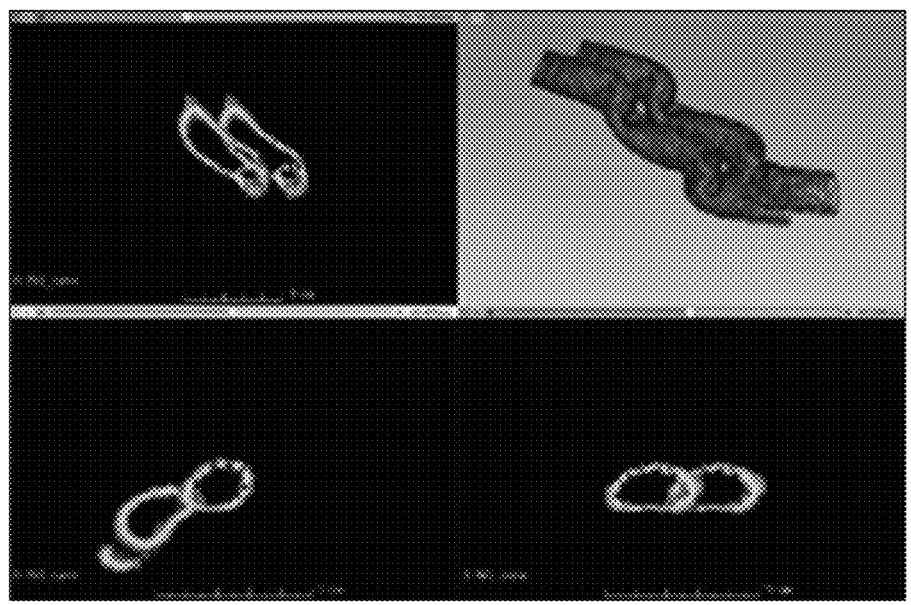

The process of construction of the different types of morphologies in blood vessels is the same as that explained above. Examples the various models are depicted in FIGS. 7-10. As shown these are 3D synthetic models (upper right of each image) and their corresponding projections (upper left, lower right, and lower left of each image) along different planes of view. FIG. 7 is a blood vessel with a no lumen (RoundLumen−) and a linear skeleton. The control points are chosen such that they lie on the major diagonal of the unit cube; i.e. on the line x=y=z in Cartesian coordinates. FIGS. 8 and 9 are blood vessel with a single lumen having linear and non-linear structures respectively. FIG. 10 is a model of a twin. As shown from the cross-sectional views, different types of morphologies can be obtained that look similar to actual morphologies in the natural images. One way of creating these multi-vessel structures is by perturbing or shifting the sampling points of the skeleton along a random direction. As can be seen from the depictions in FIGS. 7-10 the different morphologies that occur naturally can generally be generated artificially. This serves as a viable alternative to using natural data for training convolutional networks.

While the above may be used to generate random or arbitrary vasculature models, it may be appreciated that the present approach may also be utilized to model vasculature observed in an image. For example, for an image obtained of a biological sample, at least one feature of the image may be extracted by classification, and a virtual model generated in N-dimensional (e.g., three-dimensional) Cartesian coordinates that mimics the feature or features of the biological sample in N-Dimensional shape and N-Dimensional appearance.

Methods

A study was conducted using the synthetic vasculature described above to train an artificial neural network, such as a convolutional neural network (CNN). The methodology of this study and its results are discussed below.

As may be appreciated, a CNN is a type of artificial neural network. CNNs consist of multiple neuron collections which process portions of the input image called receptive fields. The outputs are then tiled so that the input regions overlap and this in turn produces a better representation of the original image. This makes CNNs translation invariant.

A CNN is conventionally made up of different types of layers, such as: an input layer, a convolutional layer, a non-linear layer, a pooling layer; and a fully connected layer. The input layer is where the networks accept the images. The images typically consist of raw pixel values depicted by width, height and the number of channels. The convolutional layer will compute the output of the neurons that are connected to local regions in the input, each computing a dot product between their weights and a receptive field. The non-linear layer is the activation function responsible for introducing the non-linearity in the model. Various types of non-linear functions include the sigmoid, the tan h, and the rectified linear unit. The pooling layer performs a down sampling operation. The high-level reasoning in the neural network is done by fully connected layers. Their activations can be performed by simple matrix multiplication.

As discussed herein, in certain embodiments, pre-trained convolutional neural networks may be used as a feature extractor. In an implementation as part of a study, the network included weights trained on the ImageNet dataset. In this implementation, the 6th layer of the network was extracted, which was a 4096-dimensional vector as a representation of the image. This may be considered as a transfer learning model because the weights learnt from another domain are transferred to blood vessel recognition. A pre-trained neural network was used called AlexNet to extract features from the data.

In the study, an experiment was performed to show that pre-trained CNNs were efficient in representing the vascular morphology. The experiment was performed on the natural data. A portion of the data, 33%, was reserved as test data and the remainder of the data was used for training. Two models were developed. One model employed the visual bag of words (VBW) feature extraction method to extract the features. The other model used the AlexNet architecture to extract the features. A 3-class classification (one vs rest) was performed using the logistic regression classifier. The accuracy, f1-score, precision and recall calculated on the same test data are provided for comparison. The results in Table 2 show that the pre-trained convolutional neural network is a suitable choice for representation of vascular morphology.

TABLE 2

Comparison of feature extraction methodologies

| Feature extractor | Accuracy | f1-score | Precision | Recall |
|---|---|---|---|---|
| AlexNet | 91.92 | 91.93 | 91.98 | 91.92 |
| VBW | 78.38 | 77.38 | 76.71 | 78.38 |

Results

As noted above, in the study related herein, features were extracted using the AlexNet architecture which was trained on the ImageNet database. The weight parameters were used to extract the features in a feedforward manner. This is referred to as transfer learning. As previously noted, 33% of the natural data was held out as test data. All the experiments were performed on this dataset for maintaining consistency in the results.

Figure 11:
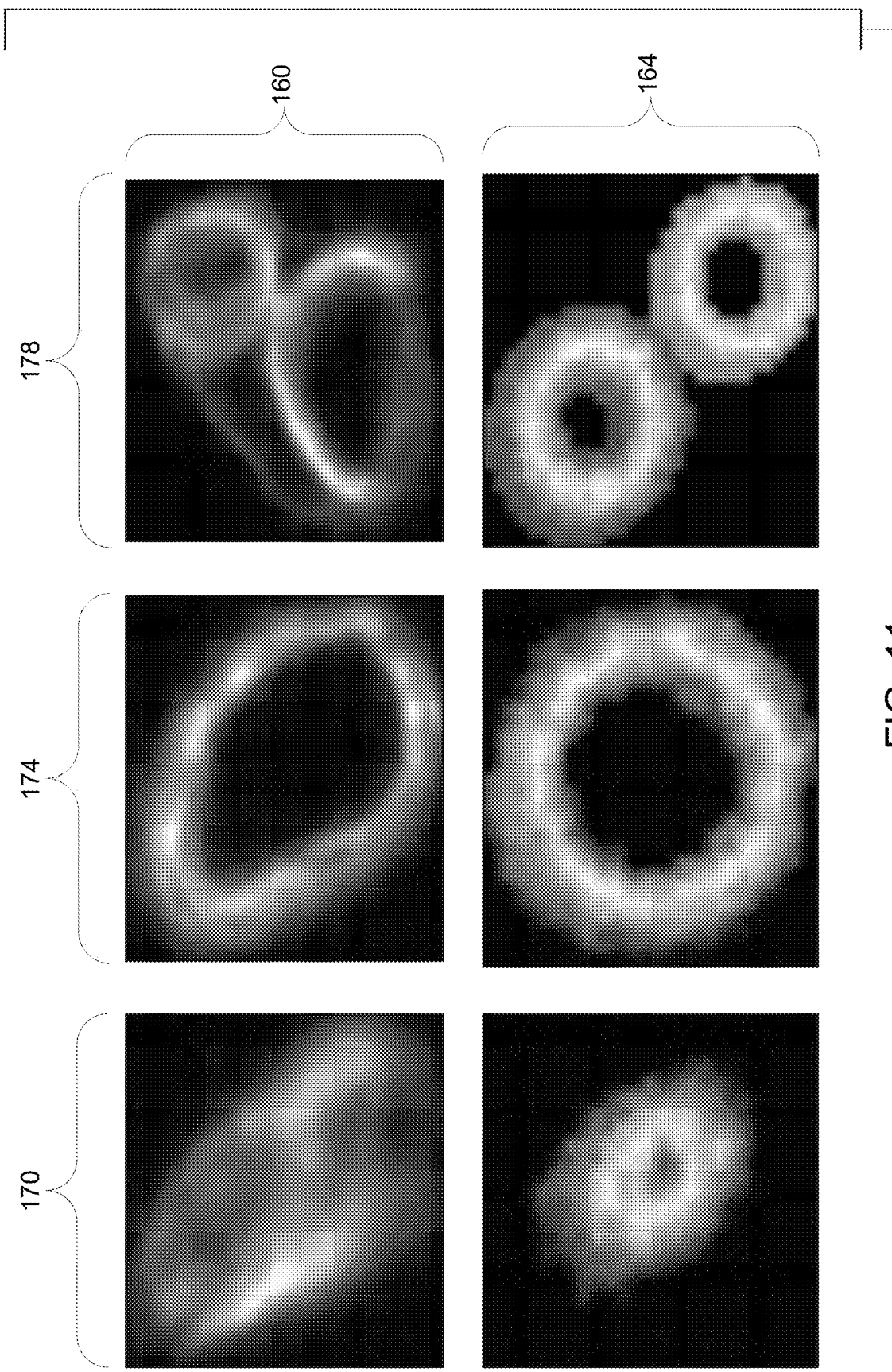
FIG. 11 depicts natural and synthetic examples of a RoundLumen−, a RoundLumen+, and a Twin, in accordance with aspects of the present disclosure.

A filtering technique was introduced to appropriately extract slices from the synthetic 3D volumes generated as described herein. This was done by obtaining the probabilities of the artificial data using a model trained on the natural training data. The probabilities of the corresponding images were then sorted and the images with the highest probabilities were selected. This provided a way to boost the artificial model by providing a larger and more robust training data set. The filtered artificial data was then used to retrain the classifier. Examples of both the natural data and synthetic data 164 are shown for comparison in FIG. 11, which depicts natural and synthetic RoundLumen− images 170, RoundLumen+ images 174, and twins 178.

A hierarchical classification was performed to first classify the single blood vessels from blood vessels that occur in pairs i.e., RoundLumen vs Twins. The second classification task involved distinguishing between RoundLumen− and RoundLumen+. This process flow is illustrated visually in FIG. 12, where as illustrated, an initial determination 192 is made with regard to a blood vessel 190 as to whether the vessel is a single vessel. If the vessel 190 is not a single vessel, in this example it is determined to be a twin 196. It the vessel 190 is determined to be a single vessel at block 192, a subsequent determination is made whether the vessel 190 has a discernible lumen at block 200. If the vessel 190 is determined to have a lumen, it is deemed to be Lumen+ 202. If the vessel 190 is determined to not have a discernible lumen, it is deemed to be Lumen− 204. AS will be appreciated, the same hierarchical classification approach may be expanded to encompass classification of other vascular structures observed in nature.

Three different types of training were performed to demonstrate the feasibility of the present approach. The first type of training was done with only the naturally occurring data. The second type of training data consisted only of the artificial data that has been filtered by the natural model as explained above. Finally, the third type consisted of both the artificial and natural training samples. This was referred to as mixed. In addition, an oversampling approach known as synthetic minority over sampling was employed to equalize the number of instances for both classes in all experiments. All the results are reported on the reserved 33% of the natural data analyzed by the three differently trained systems. The accuracy, f1-score, precision, recall and receiver operating characteristic (ROC), and precision-recall (PR) curves are reported in the following tables and figures for each of the two classification tasks.

The PR and ROC curves were calculated using the minority class in both the classification tasks, i.e., twins for the first classification task and RoundLumen− for the second task.

Figure 13:
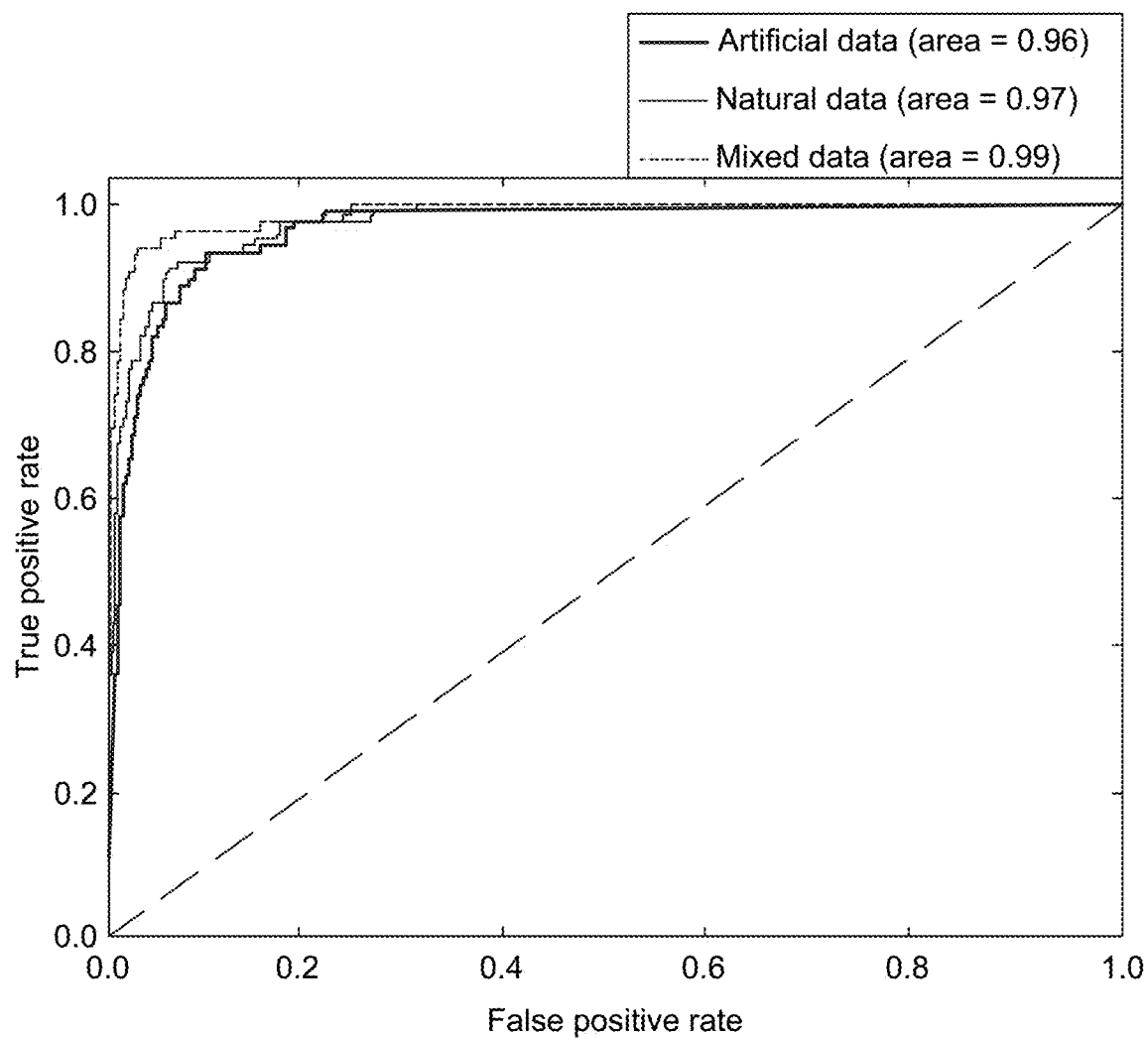
FIG. 13 is a graphical representation of a ROC curve for classification between RoundLumen and Twins, in accordance with aspects of the present disclosure.
Figure 14:
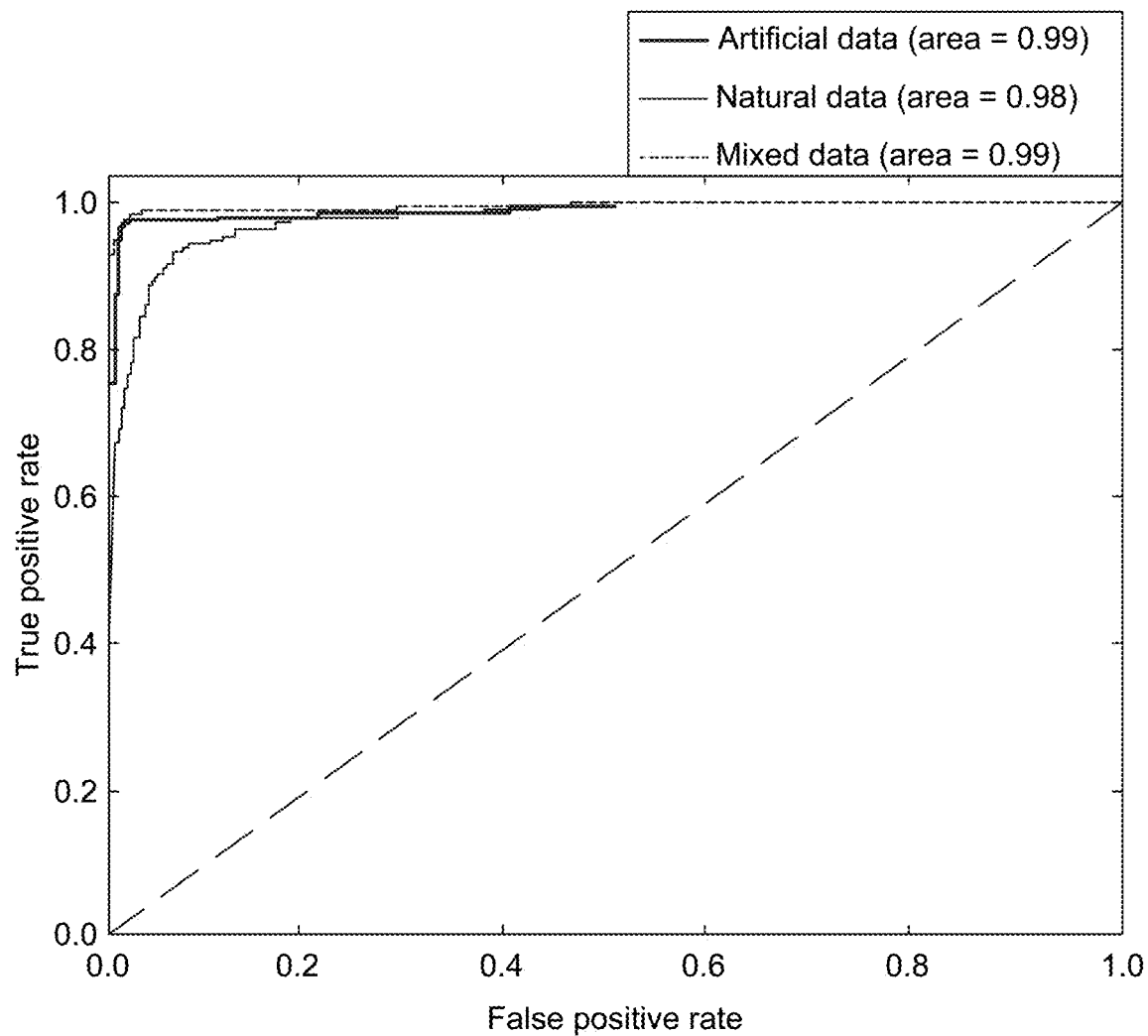
FIG. 14 is a graphical representation of precision-recall curve for classification between RoundLumen and Twins, in accordance with aspects of the present disclosure.
Figure 15:
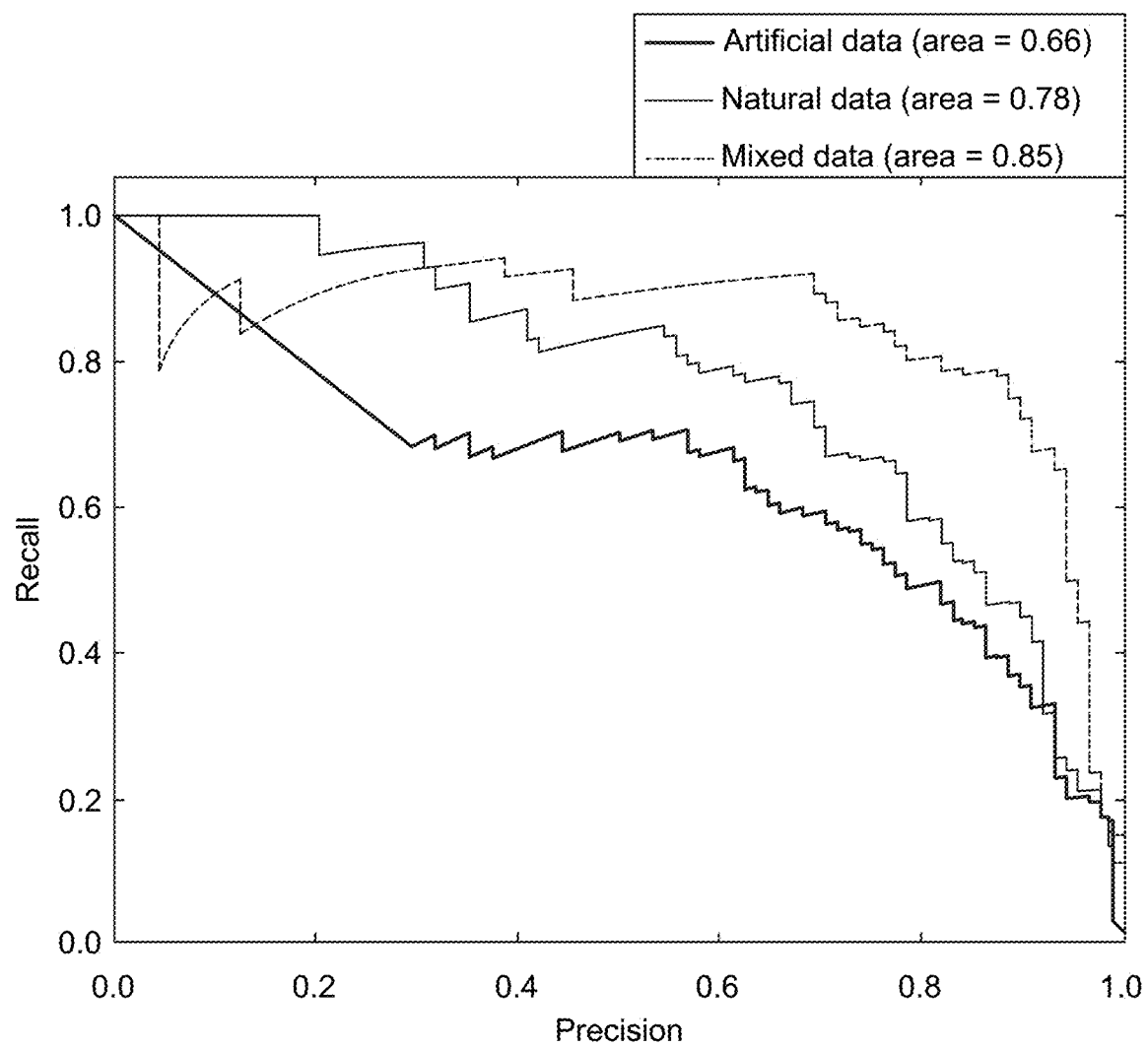
FIG. 15 is a graphical representation of a ROC curve for classification between RoundLumen− and RoundLumen+, in accordance with aspects of the present disclosure.
Figure 16:
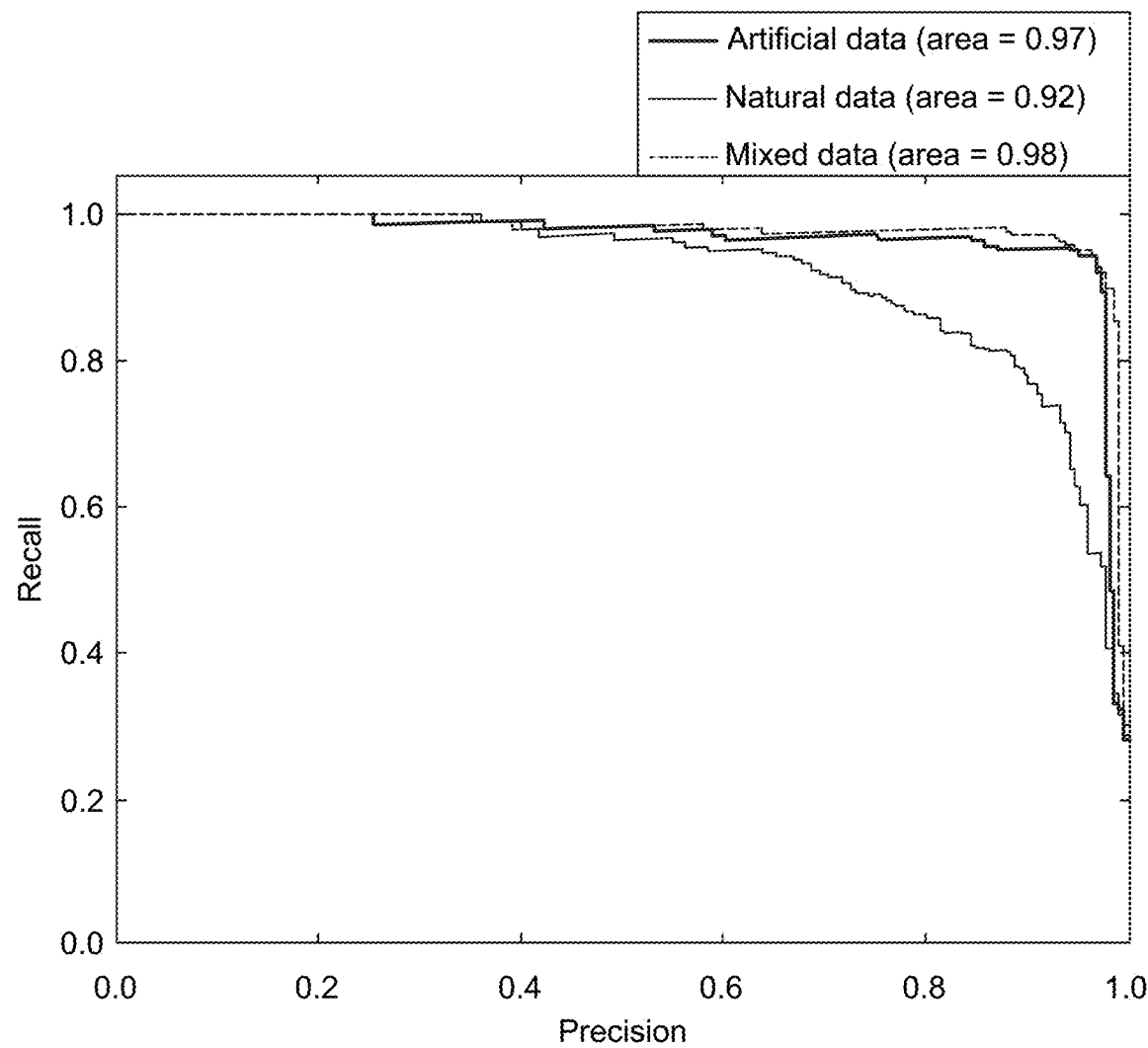
FIG. 16 is a graphical representation of a Precision-recall curve for classification between RoundLumen− and RoundLumen+, in accordance with aspects of the present disclosure.

As shown in Table 3, the synthetic vessel data captured the differences between the two classes and was also able to identify twins, which is the minority class in Task 1, from the high recall. Therefore, the results were boosted when combining both the artificial and natural data. In addition, the ROC curves for classification, shown in FIG. 13 (for single versus double blood vessels, i.e., twins) and 14 (for RoundLumen− versus RoundLumen+), and the precision recall (PR) curves, shown in FIG. 15 (for single versus double blood vessels, i.e., twins) and 16 (for RoundLumen− versus RoundLumen+), confirm that synthetic data may be successfully employed for building the models as discussed herein. In particular, as shown from the ROC and PR curves, the model built from the mixed data improved the performance of the naturally trained model.

TABLE 3

Results of binary classification between RoundLumen and Twin

| Data | Accuracy | F1-score | Precision | Recall |
|---|---|---|---|---|
| Artificial | 92.81 | 59.36 | 45.24 | 86.36 |
| Natural | 96.34 | 71.03 | 68.42 | 73.86 |
| Mixed | 97.71 | 81.76 | 79.57 | 84.01 |

Figure 12:
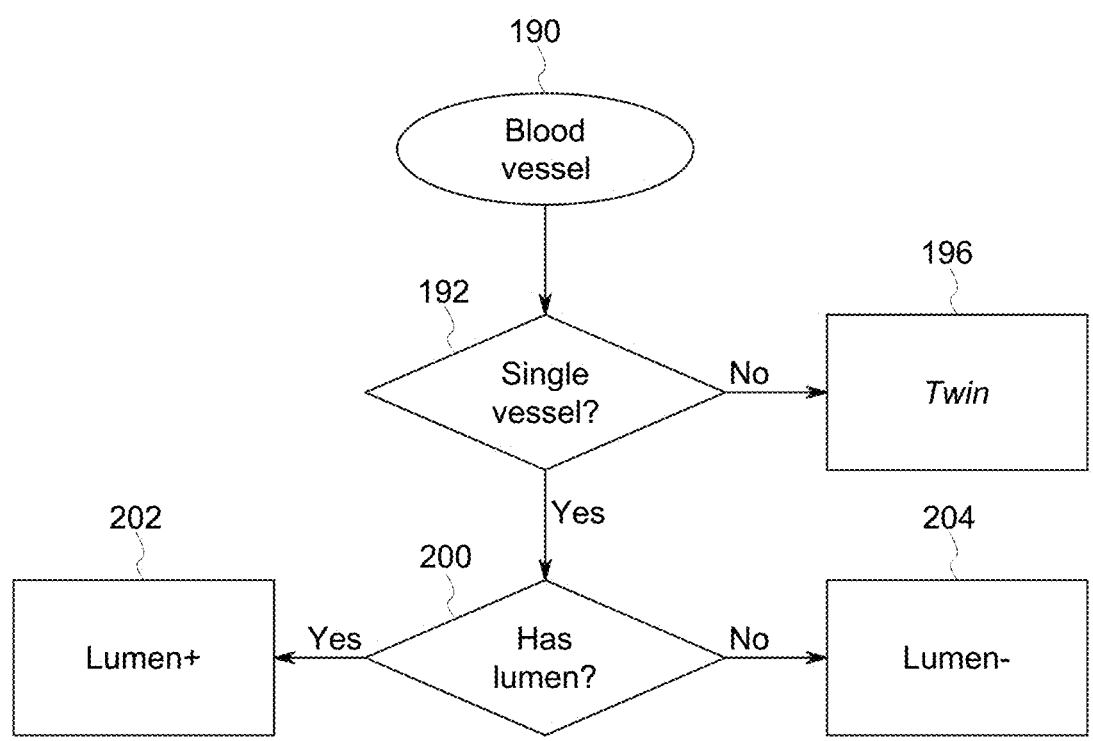
FIG. 12 is a flowchart of a hierarchical classification scheme, in accordance with aspects of the present disclosure.

Table 4 and FIGS. 10 and 12 are the corresponding results table and ROC, PR curves for the second classification task. The data shows that the synthetic data performed even better than the natural data and was able to boost the performance when trained on its own or in unison with the natural data.

TABLE 4

Results of binary classification between RoundLumen− and RoundLumen+

| Data | Accuracy | F1-score | Precision | Recall |
|---|---|---|---|---|
| Natural | 94.55 | 96.72 | 96.89 | 96.55 |
| Artificial | 98.38 | 99.02 | 99.38 | 98.67 |
| Mixed | 98.60 | 99.16 | 99.29 | 99.03 |

Figure 17:
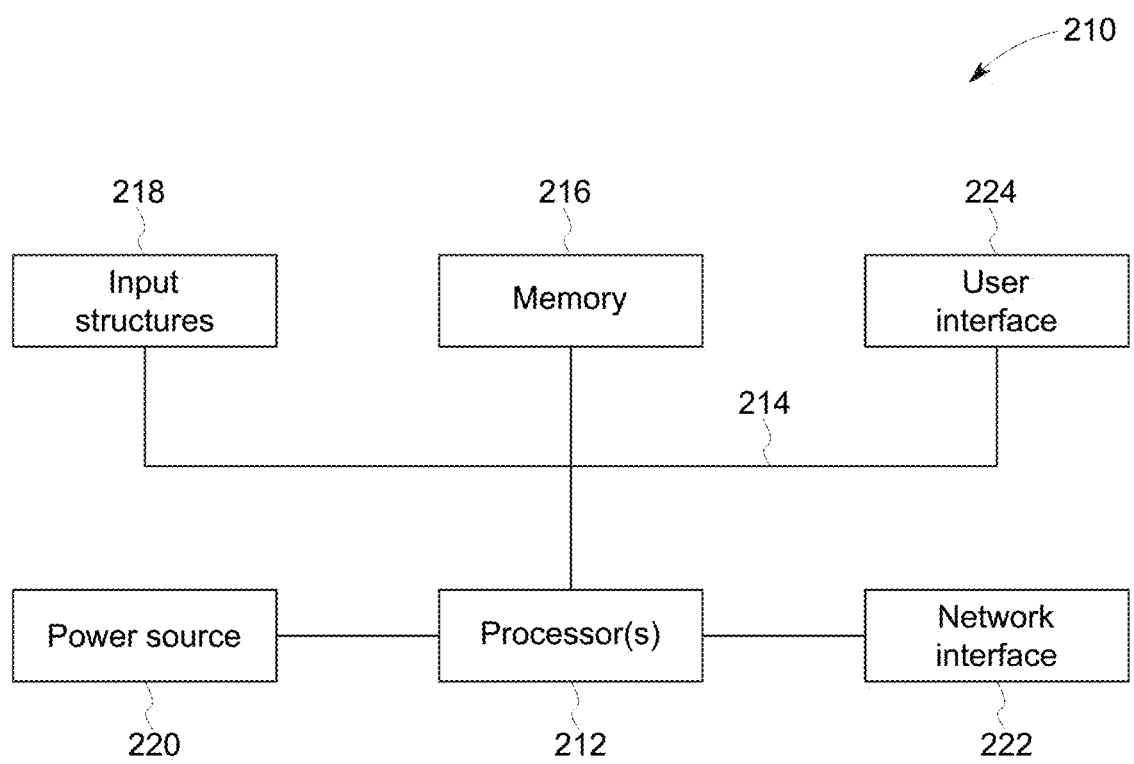
FIG. 17 is a block diagram of a computing device capable of implementing the present approach, in accordance with aspects of the present disclosure.

As will be appreciated some or all of the approach discussed herein related to data synthesis or augmentation and/or feature classification using trained artificial neural networks may be performed or otherwise implemented using a processor-based system such as shown in FIG. 17 or several such systems in communication with one another. Such a system may include some or all of the computer components depicted in FIG. 17. FIG. 17 generally illustrates a block diagram of example components of a computing device 210 and their potential interconnections or communication paths, such as along one or more busses. As used herein, a computing device 210 may be implemented as one or more computing systems including laptop, notebook, desktop, tablet, or workstation computers, as well as server type devices or portable, communication type devices, and/or other suitable computing devices.

As illustrated, the computing device 210 may include various hardware components, such as one or more processors 212, one or more busses 214, memory 216, input structures 218, a power source 220, a network interface 222, a user interface 224, and/or other computer components useful in performing the functions described herein.

The one or more processors 212 are, in certain implementations, microprocessors configured to execute instructions stored in the memory 216 or other accessible locations. Alternatively, the one or more processors 212 may be implemented as application-specific integrated circuits (ASICs), field-programmable gate arrays (FPGAs), and/or other devices designed to perform functions discussed herein in a dedicated manner. As will be appreciated, multiple processors 212 or processing components may be used to perform functions discussed herein in a distributed or parallel manner.

The memory 216 may encompass any tangible, non-transitory medium for storing data or executable routines, including volatile memory, non-volatile memory, or any combination thereof. Although shown for convenience as a single block in FIG. 17, the memory 216 may actually encompass various discrete media in the same or different physical locations. The one or more processors 212 may access data in the memory 216 via one or more busses 214.

The input structures 218 are used to allow a user to input data and/or commands to the device 210 and may include mice, touchpads, touchscreens, keyboards, and so forth. The power source 220 can be any suitable source for providing power to the various components of the computing device 210, including line and battery power. In the depicted example, the device 210 includes a network interface 222. Such a network interface 222 may allow communication with other devices on a network using one or more communication protocols. In the depicted example, the device 210 includes a user interface 224, such as a display configured to display images or date provided by the one or more processors 212.

Technical effects of the invention include generating virtual multi-dimensional data from a parametric representation, such as of vasculature in the present examples, using pre-trained convolutional neural networks. In certain embodiments, the multi-dimensional data may be three dimensional. Use of the pre-trained convolutional neural networks the steps of image segmentation and/or hand engineered feature extraction to be omitted. Thus in certain embodiments, a method to characterize the morphology is provided by taking both the shape and intensity information into account.

While only certain features of the invention have been illustrated, and described herein, many modifications and changes will occur to those skilled in the art. It is, therefore, to be understood that the appended claims are intended to cover all such modifications and changes as fall within the scope and spirit of the invention.

What is claimed is:

1. A method for generating a multi-dimensional synthetic vascular model, comprising:
   defining a set of control points in a three-dimensional coordinate system;
   interpolating between the set of control points to generate a center line of a synthetic blood vessel being generated; and
   generating a three-dimensional volume of the synthetic blood vessel utilizing the center line as input by:
      defining an inner radius of the synthetic blood vessel and an outer radius of the synthetic blood vessel; and
      defining a respective hollow disk at each of a plurality of sampling points along the center line based on the inner radius and the outer radius.

2. The method of claim 1, further comprising generating a plurality of two-dimensional images corresponding to slices taken through the synthetic blood vessel or other synthetic blood vessels of the synthetic vascular model at varying angles and orientations.

3. The method of claim 2, further comprising filtering the plurality of two-dimensional images to correspond to a naturally-occurring variability of morphological features.

4. The method of claim 1, wherein interpolating between the set of control points comprises interpolating between control points of the set using a three-dimensional cubic spline interpolator.

5. The method of claim 1, wherein a first portion of the plurality of sampling points is defined along the center line, wherein a second portion of the plurality of sampling points is defined in a radial direction relative to the center line, and wherein generating the three-dimensional volume about the center line further comprises defining an intensity with respect to the center line.

6. The method of claim 1, wherein the respective hollow disk is defined by randomly perturbing values of the inner radius and the outer radius.

7. The method of claim 1, comprising rotating the respective hollow disk along the center line by multiplying coordinates of points on the respective hollow disk by a rotation matrix.

8. A method for training and using an artificial neural network, comprising:
generating a synthetic vascular model by:
defining a set of control points in a three-dimensional coordinate system;
interpolating between the set of control points to generate a center line of a synthetic vessel being generated; and
generating a three-dimensional volume of the synthetic vessel utilizing the center line as input by:
defining an inner radius of the synthetic vessel and an outer radius of the synthetic vessel; and
defining a respective hollow disk at each of a plurality of sampling points along the center line based on the inner radius and the outer radius;
generating a training data set of images, wherein at least a portion of the images are derived by taking slices through one or more synthetic vessels of the synthetic vascular model;
providing the training data set of images to the artificial neural network to generate a trained neural network;
providing an input set of clinical images to the trained neural network for classification of vascular features within the input set of clinical images; and
receiving an output from the trained neural network based on the classifications generated for the input set of clinical images.

9. The method of claim 8, wherein the training data set is composed entirely of images derived by taking slices through one or more synthetic vessels of the synthetic vascular model.

10. The method of claim 8, wherein the training data set is composed partly of images derived by taking slices through one or more synthetic vessels of the synthetic vascular model and partly of non-synthetic vessel images.

11. The method of claim 8, wherein the artificial neural network comprises a convolutional neural network.

12. The method of claim 8, comprising filtering the training data set to exhibit morphological variability consistent with natural occurrence of the vascular features to be classified before providing the training data set to the artificial neural network.

13. The method of claim 8, wherein the trained neural network classifies the vascular features hierarchically such that an initial determination is made as to whether a respective vessel is a single vessel or not and, if the vessel is classified as a single vessel, whether a lumen is discernible or not.

14. The method of claim 8, wherein the input set of clinical images comprises fluorescence microscopy images of brain tissue.

15. A vascular morphology classification neural network, comprising:
an input layer configured to receive images depicting sectional views of one or more vascular vessels in a biological sample;
two or more hidden layers trained using synthetic vessel images from a synthetic vascular model to classify morphological features present in the sectional views of the biological sample, wherein the synthetic vascular model is generated by:
defining a set of control points in a three-dimensional coordinate system;
interpolating between the set of control points to generate a center line of a synthetic vessel being generated; and
generating a three-dimensional volume of the synthetic vessel utilizing the center line as input by:
defining an inner radius of the synthetic vessel and an outer radius of the synthetic vessel; and
defining a respective hollow disk at each of a plurality of sampling points along the center line based on the inner radius and the outer radius; and
an output layer downstream from the two or more hidden layers, wherein the output layer is configured to provide an output based on the classifications generated for the morphological features.

16. The vascular morphology classification neural network of claim 15, wherein the morphological features are classified as being one of a plurality of feature types.

17. The vascular morphology classification neural network of claim 15, wherein the act of classifying is performed hierarchically such that an initial determination is made as to whether a respective vessel is a single vessel or not and, if the vessel is classified as a single vessel, whether a lumen is discernible or not.

18. The vascular morphology classification neural network of claim 15, wherein the images provided to the input layer comprise fluorescence microscopy images of brain tissue.

19. The vascular morphology classification neural network of claim 15, wherein the two or more hidden layers are trained using only the synthetic vessel images.

20. The vascular morphology classification neural network of claim 15, wherein the two or more hidden layers are trained using a mixture of the synthetic vessel images and non-synthetic vessel images.

* * * * *